United States Patent
Lineaweaver

(10) Patent No.: US 10,183,164 B2
(45) Date of Patent: Jan. 22, 2019

(54) STIMULATION PARAMETER OPTIMIZATION

(71) Applicant: Cochlear Limited, Macquarie University, NSW (AU)

(72) Inventor: Sean Lineaweaver, Gig Harbor, WA (US)

(73) Assignee: Cochlear Limited, Macquarie University (AU)

( * ) Notice: Subject to any disclaimer, the term of this patent is extended or adjusted under 35 U.S.C. 154(b) by 62 days.

(21) Appl. No.: 15/157,636

(22) Filed: May 18, 2016

(65) Prior Publication Data

US 2017/0056655 A1    Mar. 2, 2017

Related U.S. Application Data

(60) Provisional application No. 62/210,498, filed on Aug. 27, 2015.

(51) Int. Cl.
*A61N 1/36* (2006.01)

(52) U.S. Cl.
CPC ..... *A61N 1/36032* (2013.01); *A61N 1/36036* (2017.08)

(58) Field of Classification Search
None
See application file for complete search history.

(56) References Cited

U.S. PATENT DOCUMENTS

| | | | |
|---|---|---|---|
| 4,532,930 A | 8/1985 | Crosby et al. | |
| 6,157,861 A * | 12/2000 | Faltys | A61N 1/36036 607/57 |
| 6,435,878 B1 * | 8/2002 | Reynolds | G09B 5/065 434/219 |
| 6,674,862 B1 * | 1/2004 | Magilen | A61B 5/121 381/60 |
| 7,315,761 B2 * | 1/2008 | De Ridder | A61N 1/00 600/25 |
| 8,559,645 B2 | 10/2013 | Corona-Strauss et al. | |
| 9,242,067 B2 * | 1/2016 | Shore | A61M 21/02 |
| 2002/0019668 A1 | 2/2002 | Stockert et al. | |
| 2007/0003077 A1 | 1/2007 | Pedersen et al. | |
| 2007/0223752 A1 | 9/2007 | Boretzki et al. | |
| 2010/0196861 A1 | 8/2010 | Lunner | |
| 2012/0316454 A1 | 12/2012 | Carter | |
| 2013/0230182 A1 | 9/2013 | Hannemann et al. | |
| 2014/0146987 A1 | 5/2014 | Pontoppidan et al. | |
| 2014/0369537 A1 | 12/2014 | Pontoppidan et al. | |

(Continued)

FOREIGN PATENT DOCUMENTS

WO    2012072141 A1    6/2012

OTHER PUBLICATIONS

K Strelnikov et al. Visual activity predicts auditory recovery from deafness after adult cochlear implantation, Brain 2013: 136; pp. 3682-3695.*

(Continued)

*Primary Examiner* — Brian T Gedeon

(74) *Attorney, Agent, or Firm* — Edell, Shapiro & Finnan, LLC

(57) ABSTRACT

Presented herein are techniques for optimizing stimulation parameters for use in a stimulating auditory prosthesis based on a recipient's cognitive auditory ability.

30 Claims, 6 Drawing Sheets

(56) References Cited

U.S. PATENT DOCUMENTS

2016/0283847 A1* 9/2016 Keohane .................. G06N 5/04

OTHER PUBLICATIONS

Me Doucet et al. Cross-Modal reorganization and speech perception in cochlear implant users. Brain, vol. 129, Issue 12, Dec. 1, 2006, pp. 3376-3383.*

Julia Campbell, et al., "Cross-Modal Re-Organization in Adults with Early Stage Hearing Loss", Plos One, vol. 9, Issue 2, Feb. 2014, pp. 1-8.

Kristi A. Buckely, et al., "Cross-Modal Plasticity and Speech Perception in Pre- and Postlingually Deaf Cochlear Implant Users", Lippincott Williams & Wilkins, 2010, pp. 1-14.

International Search Report and Written Opinion in counterpart International Application No. PCT/IB2016/054980, dated Nov. 21, 2016, 11 pages.

* cited by examiner

STIMULATION PARAMETER OPTIMIZATION

CROSS REFERENCE TO RELATED APPLICATIONS

This application claims priority to U.S. Provisional Application No. 62/210,498 entitled "Stimulation Parameter Optimization," filed Aug. 27, 2015, the content of which is hereby incorporated by reference herein.

BACKGROUND

Field of the Invention

The present invention relates generally to optimization of stimulation parameters in electrically-stimulating auditory prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a method is provided. The method comprises: assessing a cognitive auditory ability of a recipient of a stimulating auditory prosthesis; and determining, based on results of the assessment of the cognitive auditory ability of a recipient, a plurality of stimulation parameters for use by the stimulating auditory prosthesis, wherein the stimulation parameters are correlated to the cognitive auditory ability of the recipient.

In another aspect, a method is provided. The method comprises: performing an assessment of an individual's cognitive auditory ability; and generating, based on the assessment of the individual's cognitive auditory ability, an auditory ability profile representing an impact of cross modal reorganization on the individual's ability to process information received via a stimulating auditory prosthesis.

In another aspect, an apparatus is provided. The apparatus comprises: a memory; and one or more processors configured to: obtain one or more evaluations of a cognitive auditory ability of a recipient of a stimulating auditory prosthesis, generate, based on the assessment of the individual's cognitive auditory ability, an auditory ability profile representing an impact of cross modal reorganization on the individual's ability to process information received via the stimulating auditory prosthesis, and analyze the auditory ability profile to select a plurality of stimulation parameters for use by the stimulating auditory prosthesis, wherein the stimulation parameters are correlated to the cognitive auditory ability of the recipient.

BRIEF DESCRIPTION OF THE DRAWINGS

Embodiments of the present invention are described herein in conjunction with the accompanying drawings, in which.

DETAILED DESCRIPTION

Embodiments of the present invention are generally directed to techniques for optimizing stimulation parameters for use in a stimulating auditory prosthesis based on a recipient's cognitive auditory ability. As used herein, a recipient's "cognitive auditory ability" refers to the functional operation of the recipient's auditory brain areas when processing sound inputs, including how the recipient's brain analyzes, categorizes, and interprets meaningful sounds, particularly under substantial degradation; how contextual cues facilitate this process, including semantic context and how simple temporal or spectral regularities of sound shape the neural processing; and how cognitive mechanisms compensate for degraded sound processing ability, including executive functions such as working memory and cognitive control that support successful coping with degradation.

As described further below, embodiments of the present invention are specifically directed to adapting a cochlear implant stimulation program (stimulation parameters) to a recipient's objectively determined (or semi-objectively determined) cognitive auditory ability (cognitive auditory status). In general, the cochlear implant stimulation parameters are tailored to the recipient's cognitive auditory abilities so as to provide as much auditory information as a recipient can reasonably process and accordingly benefit therefrom. This will change over time as a recipient's abilities increase or decrease (e.g., organically, abetted by rehabilitation/training, or due to progression of a disorder). The time window for making program changes within the context of the embodiments presented herein are on the order of weeks, months, and years. As such, the techniques presented herein enable a recipient's stimulation parameters to be refined and adapted as the recipient's cognitive auditory ability improves (e.g., through rehabilitation/training) or regresses (e.g., due to aging).

There are several types of stimulating auditory prostheses that operate by delivering electrical/current stimulation signals to a recipient so as to compensate for a deficiency in the recipient's nerves, tissue, etc. Merely for ease of illustration, the techniques presented herein are primarily described herein with reference to one type of stimulating auditory prosthesis, namely a cochlear implant. It is to be appreciated that techniques presented herein may be used with other stimulating auditory prostheses (e.g., auditory brainstem stimulators) or other implantable tissue-stimulating systems that include, for example visual prostheses.

Figure 1:
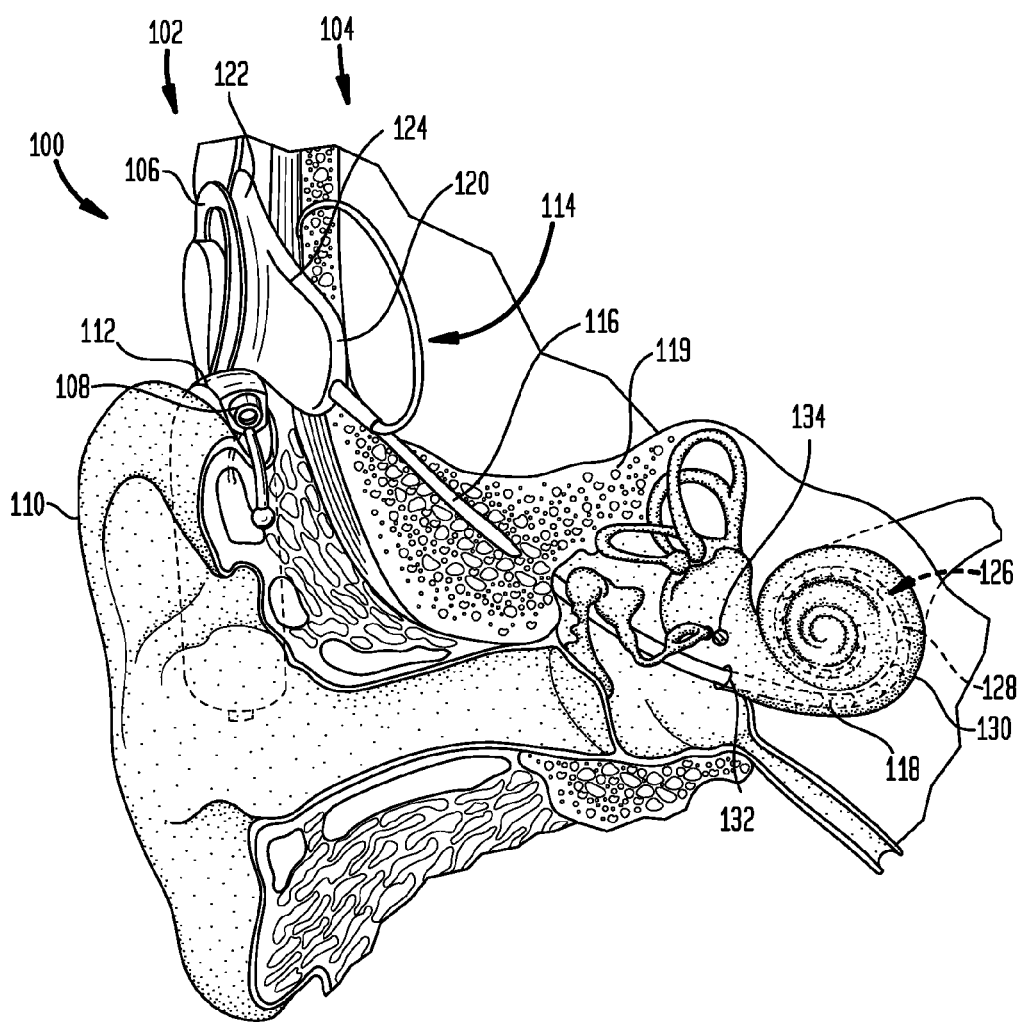
FIG. 1 is a schematic diagram illustrating a cochlear implant system configured to operate using correlated stimulation parameters generated in accordance with embodiments presented herein.

FIG. 1 is schematic diagram of an exemplary cochlear implant system 100 configured to operate using stimulation parameters optimized based on a recipient's cognitive auditory ability in accordance with embodiments of the present invention. The cochlear implant system 100 comprises an external component 102 and an internal/implantable component 104. In this example, the implantable component 104 is a cochlear implant.

The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound signals or input audio signals, and a sound processing unit 112. The sound processing unit 112 includes, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1).

The cochlear implant 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and cochlear implant 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to a cochlear implant and, as such, FIG. 1 illustrates only one example arrangement.

Elongate stimulating assembly 118 is configured to be at least partially implanted in cochlea 130 and includes a plurality of longitudinally spaced intra-cochlear electrical stimulating contacts (electrical contacts) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal that represents the detected sound signals. Since these encoded data are used by the cochlear implant 104 to generate stimulation signals, and because these signals vary dynamically according to the sound signals, the encoded data signals generated by the sound processor are sometimes referred to herein as "processed audio signals."

The processed audio signals generated by the sound processor are provided to the stimulator unit 120 via the RF link between the external coil 106 and the internal coil 122. The stimulator unit 120 includes one or more circuits that converts the processed audio signals, received via the transceiver unit 124, into sets of electrical stimulation signals (current stimulation) that are delivered via one or more stimulation channels that terminate in the stimulating contacts 128 (i.e., the sets stimulation signals are delivered to the recipient via the stimulating contacts 128). In this way, cochlear implant system 100 stimulates the recipient's auditory nerve cells, bypassing absent or defective hair cells that normally transduce acoustic vibrations into neural activity. Each set of stimulation signals represents a "stimulation cycle" that provides audio information to the recipient.

The stimulator unit 120 uses a variety of pre-determined recipient-specific stimulation parameters/settings to convert the processed audio data into one or more sets of stimulation signals. These stimulation parameters include, for example, channel-to-electrode mappings, stimulation/pulse rate, pulse timing (electrical pulse width and inter-pulse gap), mode of stimulation (polarity, reference electrode), compression law or compression settings, amplitude mappings, etc. Amplitude mapping refers to the mapping of a sound intensity to a current level that is between the recipient's threshold (T) level (i.e., the level at which he/she can just hear the stimulus) and the maximum comfortable (C) level. In general, the stimulation parameters dictate how the processed audio signals are used for generation of sets of stimulation signals (current pulses) for delivery to the recipient.

The human brain is organized into different areas of specialization that are each typically dedicated to relatively higher functions of brain activity. For example, the sensory areas of the brain (sensory brain areas) collectively refer to the region of the cerebral cortex that is associated with the receiving and interpreting of sensory information from various parts of the body. The sensory areas of the brain include somatic, auditory, visual, and olfactory cortical areas/regions. The auditory areas of the brain (auditory brain areas), in particular, are the parts of the brain that process sound information relayed thereto by the cochlea and auditory nerve.

Individuals who experience sensory deprivation will generally underutilize the sensory areas of their brain that are associated with the deprived sense. For example, an individual suffering from a hearing impairment may lack the ability to fully utilize the functional abilities of the auditory brain areas. The human brain is adaptable such that, when underutilization of a specific sensory area occurs, the brain will reorganize as a result of the underutilization.

For instance, congenitally blind research subjects have shown an enhanced ability to perform both auditory tasks, meaning that visual brain areas have reorganized for enhancement of the subject's hearing. This physiological phenomenon, sometimes referred to herein as cross modal brain reorganization or, more simply, cross modal reorganization, is most notably observed in early development (i.e., less than 7 years old) when neural plasticity is most prevalent, but this physiological phenomenon continues to a lesser degree into adulthood.

Although cross modal reorganization enhances behavioral performance for the recruiting modality, the cross modal reorganization also diminishes performance of the recruited modality. In other words, reorganizing from a less utilized brain area to enhance another sense negatively affects the less utilized brain area because it depletes the resources available to the less utilized area. For example, reorganizing the auditory brain areas in a sound deprived (deaf or partially deaf) individual in order to bolster visual ability results in greater auditory impairment. Therefore, if auditory information is later introduced through, for example, a cochlear implant, an individual who has experienced reorganization of the auditory brain areas as a result of their hearing impairment will find it more difficult to process the auditory information, when compared to an individual who as not experienced the same degree of cross modal reorganization. This is because the reorganized auditory brain areas have fewer or sub-optimally tuned cortical resources for use in processing the auditory information. Fewer cognitive resources results in a reduced cognitive capacity, which results increased in either cognitive load and/or listening effort.

Cross modal reorganization and associated deprivation of the auditory brain areas may manifest in different forms and occur for different reasons, leading to different auditory cognitive capacities/abilities in different recipients. As such, the performance of cochlear implants varies across the recipient population due, at least in part, to different cognitive auditory abilities. Accordingly, presented herein are techniques for selecting/determining stimulation parameters based on a recipient's cognitive auditory ability/capacity. In other words, the techniques presented herein determine cochlear implant stimulation parameters that are optimized/tailored to a recipient's unique cognitive auditory ability.

Figure 2:
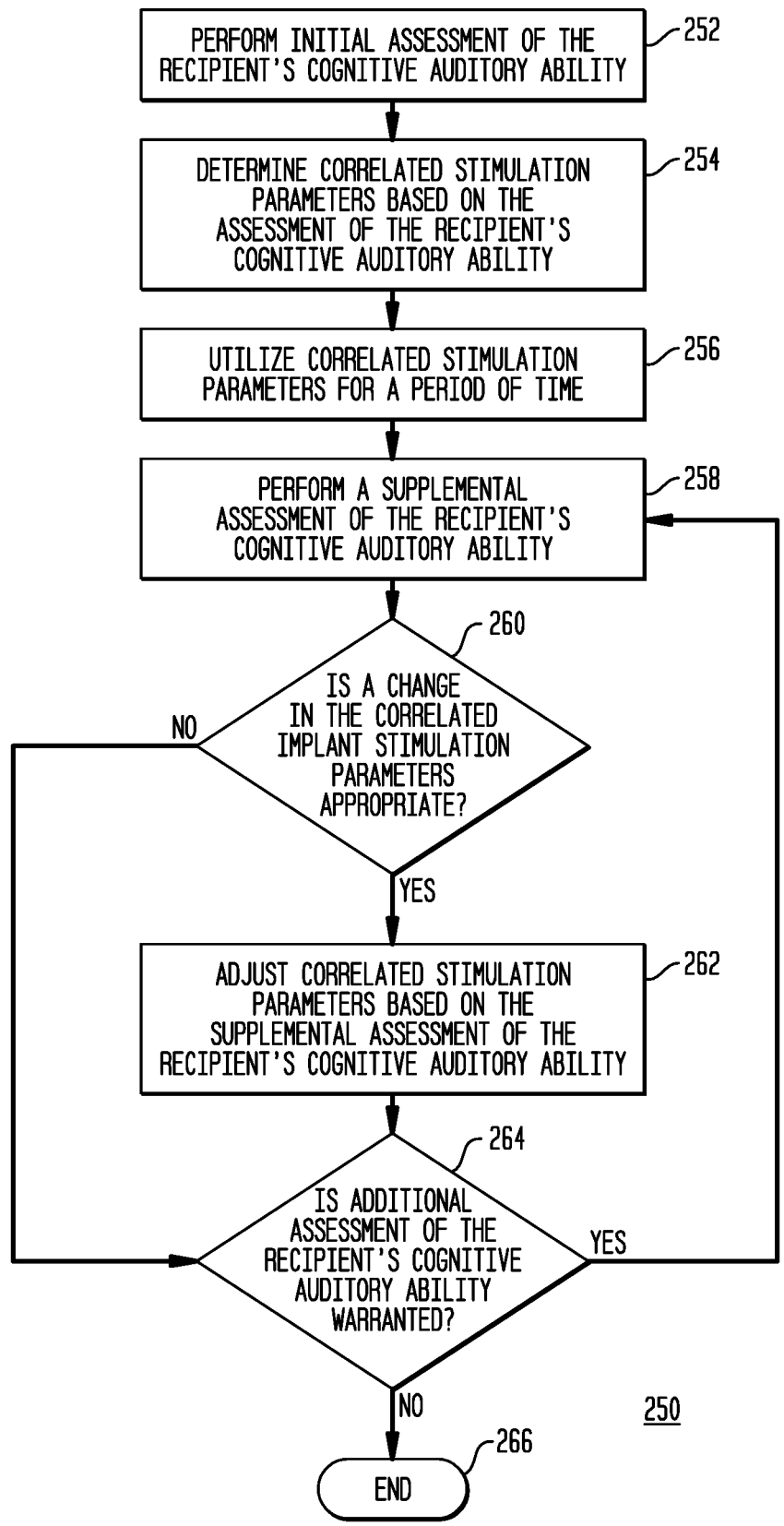
FIG. 2 is a detailed flowchart of a method in accordance with embodiments presented herein.

FIG. 2 is a flowchart of a detailed method 250 in accordance with embodiments presented herein. For ease of illustration, method 250 is described with reference to cochlear implant system 100 of FIG. 1.

Method 250 begins at 252 with the initial assessment of the cognitive auditory capacity/ability of a cochlear implant recipient. There are, in general, two methodological classes of tests/evaluations used to identify cognitive auditory ability, namely objective evaluations and subjective evaluations. Therefore, the initial assessment of the recipient's cognitive auditory ability may include one or more objective and/or subject evaluations that generate information useable to identify cross modal reorganization and to determine an estimated impact of the cross modal reorganization on a recipient's hearing capabilities.

Objective evaluations of cognitive auditory ability include, for example, functional near-infrared spectroscopy (fNIRS), functional magnetic resonance imaging (fMRI), Magnetoencephalography (MEG), Electroencephalography (EEG), etc. of a recipient's brain to evaluate the recipient's auditory brain configuration. More specifically, an imaging system generates results useable to characterize dynamic glucose metabolism, and thus metabolic activity, in different cortical areas in response to different sensory activities. For instance, the uncompromised auditory brain areas (i.e., auditory areas of the brain that have not experienced cross modal reorganization) will demonstrate increased metabolic activity when the recipient performs listening tasks/exercises. Conversely, if the auditory areas of the brain have experienced significant cross modal reorganization to support the visual system, the auditory areas of the brain will demonstrate increased metabolic activity when the recipient performs visual tasks, but little to no activity while performing purely auditory tasks. The degree of metabolic activity detected in response to different types of stimuli (e.g., auditory, visual, etc.) is used to objectively quantify how the auditory areas of the brain have been affected by cross modal reorganization (i.e., determine how much of the auditory areas of the brain are used by other non-auditory brain functions).

When fewer dedicated resources are available for the cognitive task of listening, listening tasks becomes more difficult or taxing for a recipient. As such, subjective evaluations of cognitive auditory ability may involve assessment of cognitive load or listening effort to highlight reduced auditory cognitive capacity or increases in other sensory modalities. In one embodiment, the working memory of a cochlear implant recipient is assessed with a reading span task and a digit span task. The reading span task is a dual task paradigm in which subjects are asked to read printed sentences aloud and remember the last word of each sentence for later recall in the order presented. Following each sentence, the subject states whether the sentence is true or false. Sets range from 2 to 6 sentences in length, and at the end of each set, the subject is asked to recall the last word of each sentence. The forward or backward digit span tasks measures working memory in a similar fashion. A subject repeats lists of digits spoken in live-voice at a rate of one digit per second. The forward span task requires simply repeating back the series of digits, while the backward span task requires repeating the digits in reverse order. Two lists are presented beginning with a length of two digits and increasing in length by one digit after each successful repetition of at least one list at a given length.

It has been observed that there is a high coincidence of hearing problems and other sensory issues. As such, certain embodiments also include specific sensory tests/evaluations in the assessment of a recipient's cognitive auditory ability. Sensory evaluations, which are subjective in nature, may take a number of different forms, but are primarily designed to provide an understanding of functional sensory difficulties experienced by a recipient. Such an understanding may be important because recipients with different sensory issues are uniquely impacted in different sensory environments. In general, the sensory evaluations involve the elicitation and observation of a recipient's responses to different sensations and looking for evidence of difficulty making proper use of a sensory input.

In general, an initial assessment of a recipient's cognitive auditory ability will include both objective and subjective evaluations performed in a clinical setting. For example, a medical practitioner (e.g., doctor, audiologist, clinician, etc.) performs an EEG on the cochlear implant recipient to objectively determine the extent of cross modal reorganization. Within the same timeframe (e.g., during the same one or two week window), the cochlear implant recipient is given a cognitive load test (e.g., a reading span rest), and perhaps a sensory evaluation.

The results of the objective and subjective evaluations are correlated with one another to generate a recipient's "auditory ability profile." As used herein, a recipient's auditory ability profile represents an estimated impact of the cross modal reorganization on the recipient's ability to process information received from via stimulating auditory prosthesis. In other words, the cross modal reorganization is analyzed in conjunction with the measures of cognitive load or listening effort to assess how the recipient's auditory brain areas are able to process electrical audio information which, as described further below, enables a determination of how stimulation parameters should be selected.

Returning to the specific example of FIG. 2, at 254 the results of the initial assessment of the recipient's cognitive auditory ability, represented in the recipient's auditory ability profile, are analyzed and used to determine stimulation parameters for use in the recipient's cochlear implant 104. As noted above, the recipient's stimulation parameters are the settings/parameters that dictate how the stimulator unit 120 of the cochlear implant 100 will convert the processed audio data into stimulation signals for delivery to the recipient's cochlea 130. The stimulations signals generated and delivered to the recipient's cochlea 130 operate as a form of electrical audio information that is presented to the recipient's auditory brain areas via the cochlea nerve cells. The various stimulation parameters control the amount of electrical audio information that is presented to a recipient at any given time.

As a result of cross modal reorganization and other factors, the auditory cortices of different recipients have different abilities to process electrical audio information. Therefore, in accordance with the embodiments presented herein, the recipient's auditory ability profile is analyzed to select stimulation parameters that will generate electrical stimulation signals that, when delivered to the recipient, optimize the amount of electrical audio information presented to the recipient in view of the recipient's cognitive auditory ability (i.e., match/correlate a measure of the information expected to be presented by the stimulation parameters to the estimated ability of the recipient's auditory brain areas to process electrical audio information). In other words, the stimulation parameters are correlated to, and selected based on, the recipient's cognitive auditory ability. As used herein, stimulation parameters that are selected based on the recipient's cognitive auditory ability are referred to herein as "correlated stimulation parameters." Correlated stimulation parameters currently in use by a cochlear implant are sometimes referred to herein as the "current" or "present" correlated stimulation parameters.

At 254, the initial correlated stimulation parameters are customized for the recipient based on the recipient's cognitive auditory ability. This reflects a potential advantage over conventional techniques use for selection of a recipient's initial stimulation parameters. More specifically, as noted above, there are a large number of stimulation parameters that can be selected for a cochlear implant recipient. In conventional techniques, an audiologist selects initial stimulation parameters for a recipient based on, for example, the audiologist's clinical knowledge, parameters/programs known to be useful for other cochlear implant recipients, study results, etc. Since, in such conventional arrangements, the stimulation parameters are not at all customized to the recipient, there is a significant possibility that the selected stimulation parameters will not be acceptable to the recipient. As such, after selection of initial stimulation parameters, in conventional arrangements the audiologist and recipient undertake a time-consuming, expensive, and difficult trial-and-error process in which sounds are delivered to a recipient and, using verbal feedback, the audiologist evaluates and changes/adjusts the initial stimulation parameters. Although difficult for many recipient's, such trial-and-error processes are unworkable with young children since they lack the ability to provide the necessary feedback to the audiologist.

However, as noted above, in accordance with the embodiments presented herein, the initial correlated stimulation parameters are customized for the recipient based on the recipient's cognitive auditory ability. Therefore, there is a greater likelihood that the initial correlated stimulation parameters selected at 254 will be suited for the recipient. This reflects an advantage in that the trial-and-error processes can be eliminated (e.g., for young children) or substantially reduced since the audiologist is unlikely to have to initial significant parameter changes.

Returning to the example of FIG. 2, after the selection of the recipient's initial correlated stimulation parameters at 254, at 256 the recipient is allowed to use the correlated stimulation parameters for a period of time. In one example, the correlated stimulation parameters are used during several hearing tests conducted over a short period of time before performance of the supplemental assessment of the recipient's cognitive auditory ability (e.g., a shortened parameter evaluation process with the audiologist). In other embodiments, the recipient is allowed to use the correlated stimulation parameters over a longer period of time (e.g., several days or weeks).

At 258, a supplemental assessment of the recipient's cognitive auditory ability is performed. The supplemental assessment of the recipient's cognitive auditory ability may take a number of different forms, but generally includes one or more subjective as described above with reference to the initial assessment of the recipient's cognitive auditory ability. In accordance with embodiments presented herein, the supplemental assessment may be performed in a clinical setting or, in certain examples, in the recipient's home or other remote (i.e., non-clinical) setting. For example, at a follow-up clinical appointment, subjective evaluations are performed to identify changes in functional cognitive capacity (cognitive load). The results of the supplemental assessment are used to update the recipient's auditory ability profile (i.e., correlated with the results of previous subject and objective evaluations).

Supplemental assessments may include objective evaluations (e.g., imaging), but, in general, objective evaluations would be repeated less frequently as they are more time-consuming and potentially require more resources than subjective cognitive load evaluations. Nonetheless, correlations between the objective and subjective evaluations are checked and realigned periodically.

In certain embodiments, the supplemental assessments include subjective evaluations (e.g., cognitive load testing) that are performed in a remote (i.e., non-clinical) environment via, for example, a smart phone, computer, or other consumer electronic device. In such examples, as long as the remotely performed subjective evaluations are correlated/aligned with the subjective evaluations performed in the clinical environment, it may be possible for a recipient to initiate changes in stimulation parameters based on self-evaluations of auditory ability. Further details regarding self-evaluations are provided below with reference to FIG. 4.

The supplemental assessment (or possibly the initial assessment) may be accompanied by one or more hearing tests that objectively (e.g., Neural Response Telemetry tests relying upon electrically evoked compound action potential (ECAP) measurements) or subjectively (e.g., verbal feedback tests) evaluate the performance of the cochlear implant. Such tests are not designed to evaluate cognitive auditory ability, but instead attempt to determine how well the current correlated stimulation parameters are working for the recipient (i.e., is the recipient, when using the correlated stimulation parameters, able to understand the information that is presented at each stimulation cycle). These hearing tests may be useful in determining, for example, whether the recipient is having difficultly hearing in general, difficulty in noise, difficulty in certain frequency ranges, etc.).

After performance of the supplemental assessment of the recipient's cognitive auditory ability, at 260 the current correlated stimulation parameters are evaluated to determine if a change in the correlated stimulation parameters is appropriate. That is, the results of the supplemental assessment (i.e., the recipient's updated auditory ability profile) are utilized, possibly in conjunction with the results of the one or more other hearing tests, to determine if the correlated stimulation parameters currently in use by the cochlear implant 104 are properly correlated to the recipient's cognitive auditory ability.

Since cognitive changes, identified by subjective evaluations (task load), objective evaluations, or both, reflect the increasing or decreasing ability of cognitive resources to adequately process the information presented by the cochlear implant, 260 of FIG. 2 represents a determination of whether there has there been a long-term change in the recipient's auditory ability so as to warrant a change in stimulation parameters. If, at 260, it is determined that no changes should be made to the correlated stimulation parameters, then method 250 proceeds to 264, the operations of which are described further below. However, if it is determined at 260 that a change to the correlated stimulation parameters is warranted, then method 250 proceeds to 262 where the correlated stimulation parameters are adjusted.

More specifically, at 262, the correlated stimulation parameters are adjusted to either increase or decrease the amount of information presented through the use of the stimulation parameters. In other words, the stimulation parameters may be made more or less "information intensive" by, for example, changing the rate of stimulation, changing the number of spectral maxima, adjusting the Spectral Masking Threshold, adjustment of the Temporal Masking Offset, etc.

Certain stimulation parameters have been proven to cause greater hearing difficulties than other parameters. For instance, presenting electrical stimuli to the cochlea in a more spectrally/physiologically dense configuration is generally more difficult for the recipient to process than more sparse presentations with a better spectral contrast. Although a dense presentation provides more information to the recipient, not all recipients are capable of efficiently benefiting from it. Similarly, higher stimulation rates, although providing more information, have also been associated with listening difficulty among certain recipient (e.g., recipients often prefer programs with slower stimulation rates and fewer number of maxima) when listening to music (which can be considered as structured noise). Competitive auditory inputs (e.g., multiple speakers, music, noise, etc.) may also contribute to the creation of difficult listening conditions if not properly mitigated by stimulation parameter selection. For instance, noise reduction schemes that reduce competitive/confounding inputs are generally easier for listening because information is overload suppressed.

Therefore, in certain examples, reducing the rate of stimulation and/or the number of spectral maxima reduces the amount of information that is delivered to a recipient in each stimulation cycle while, conversely, increasing the rate of stimulation and/or the number of spectral maxima increases the amount of information that is delivered to a recipient in each stimulation cycle. The above adjustments are illustrative and it is to be appreciated that other adjustments to the stimulation parameters are possible in order to increase/decrease the amount of information that is delivered to a recipient in each stimulation cycle.

Similarly, recipients with different sensory issues perform differently in different sensory environments. Selecting stimulation parameters so as to mitigate the factors to which these recipients are sensitive will improve listening. For instance, if a recipient with sensory issues, particularly one who is sensitive to loud noises or noise in general, would likely benefit from a program that includes limits to loud amplitudes or includes noise reduction in general.

After adjustment of the correlated stimulation parameters, method 250 proceeds to 264 to determine whether or not additional assessment of the recipient's cognitive auditory ability is warranted. If additional assessment is warranted, the method 250 returns to 256 where the recipient is allowed to use the correlated stimulation parameters for a period of time before repeating steps 258-264. If it is determined that additional assessment of the recipient's cognitive auditory ability is not warranted, then method 250 ends at 266.

FIG. 2 has been described with reference to the assessment of cognitive auditory and the use of the assessment results for selecting and/or optimizing cochlear implant stimulation parameters. However, it is to be appreciated that the cognitive auditory ability assessment results may also be used to determine if an individual is a candidate for a cochlear implant. More specifically, the information gathered from pre-implantation cognitive auditory ability assessments could be used to characterize a prospective recipient's cochlear implant candidacy and/or predictive outcomes with a cochlear implant. Generally speaking, if the information gathered from pre-implantation cognitive auditory ability assessments indicate that the potential recipient has not experienced significant cross modal reorganization, then the potential recipient may have greater success with the cochlear implant.

As noted above, individuals with hearing impairments are susceptible to cross modal reorganization that detrimentally affects the auditory areas of the brain. However, the introduction of auditory inputs, such as with electrical audio information provided via a cochlear implant, can reclaim some of the recipient's previously reconfigured auditory resources and can therefore increase the recipient's cognitive auditory ability. Therefore, not only does hearing performance decline with age, but it is also possible for a recipient's hearing to improve as the brain adapts to the stimulation. As such, understanding long-term cognitive auditory ability changes (i.e., changes over weeks, months, or even years) makes it possible to prescribe dynamic stimulation strategies and/or parameters. For example, if a recipient shows that cognitive ability is on the rise, then the recipient may be able to use more aggressive stimulation parameters (e.g., higher rates, greater spectral density, etc.).

Accordingly, in addition to tailoring stimulation parameters to the recipient's present cognitive auditory ability and sensory status, it is also possible to generate a rehabilitation strategy for the recipient. For example, a recipient may be prescribed with dynamic stimulation parameters that adapt over time to provide increasingly dense spectral representations of sound in an adaptive manner designed to challenge and improve the recipient's cognitive auditory ability. In other words, the stimulation parameters may be scheduled to periodically, randomly, progressively, etc. push the limits of how much information the recipient can process, so as to recover additional resources of the auditory brain areas.

In certain examples, the rehabilitation strategy may involve auditory training sessions or periods that are specifically designed to challenge the recipient and improve auditory function. Again, these rehabilitation sessions are configured such that the auditory training tasks that occur therein are modified in accordance with the recipient's cognitive auditory ability and may be updated as the auditory ability improves.

When performing rehabilitation, the recipient's response to auditory training sessions or periods may be monitored over a period of time to see if any improvement has occurred. If improvement is detected, stimulation parameters that provide a greater amount of information may be selected.

Figure 3:
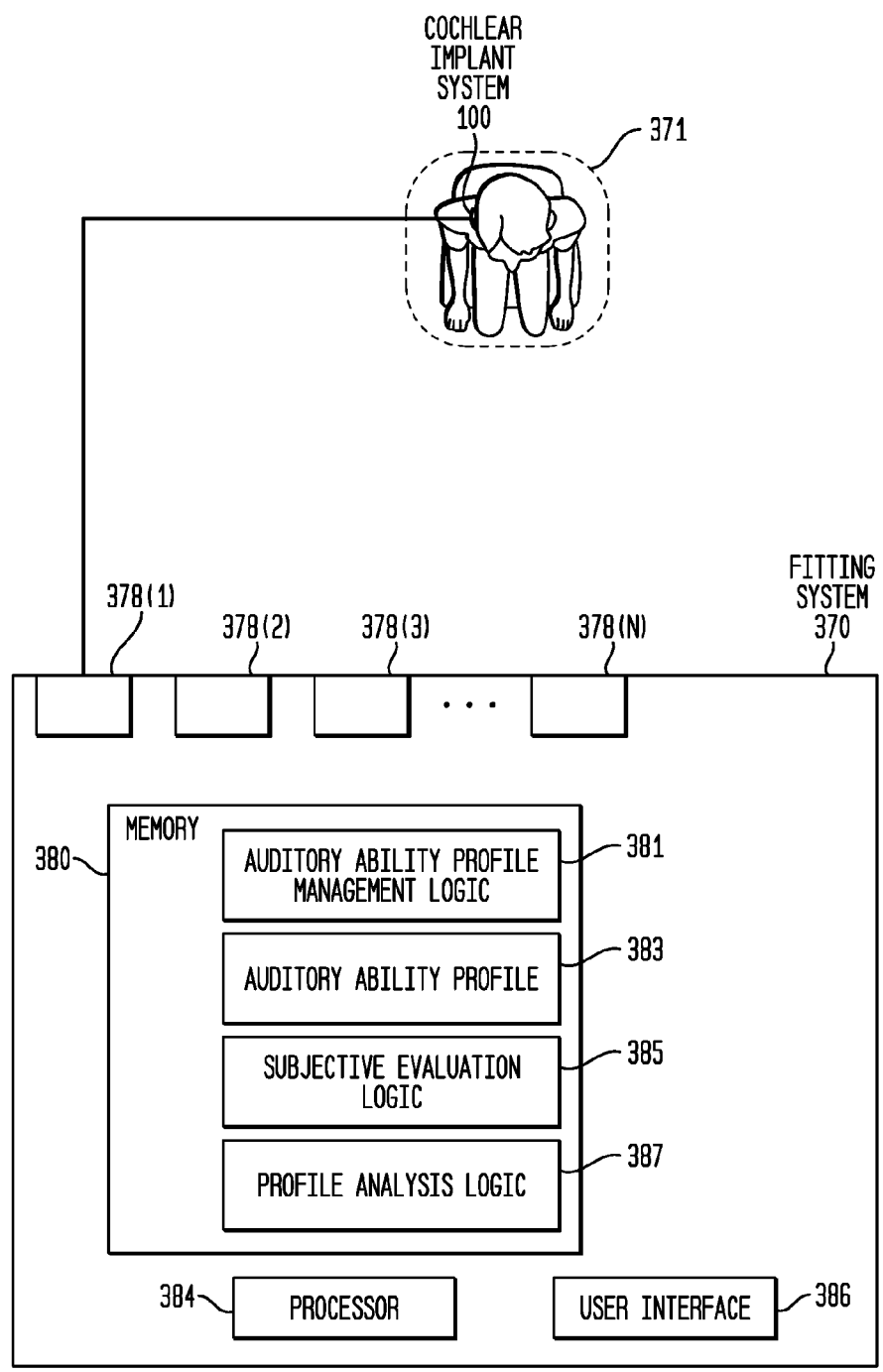
FIG. 3 is a block diagram of a fitting system configured to execute techniques in accordance with embodiments of the present invention.

As noted above, method 250 includes both an initial assessment of a recipient's cognitive auditory ability and one or more supplemental assessments of a recipient's cognitive auditory ability. Also as noted above, the initial assessment of a recipient's cognitive auditory ability is generally performed in a clinical environment since the initial assessment includes both objective and subjective evaluations. FIG. 3 is block diagram illustrating an example fitting system 370 configured to execute the techniques presented herein.

Fitting system 370 is, in general, a computing device that comprises a plurality of interfaces/ports 378(1)-378(N), a memory 380, a processor 384, and a user interface 386. The interfaces 378(1)-378(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 3, interface 378(1) is connected to cochlear implant system 100 having components implanted in a recipient 371. Interface 378(1) may be directly connected to the cochlear implant system 100 or connected to an external device that is communication with the cochlear implant systems. Interface 378(1) may be configured to communicate with cochlear implant system 100 via a wired or wireless connection (e.g., telemetry, Bluetooth, etc.).

The user interface 386 includes one or more output devices, such as a liquid crystal display (LCD) and a speaker, for presentation of visual or audible information to a clinician, audiologist, or other user. The user interface 386 may also comprise one or more input devices that include, for example, a keypad, keyboard, mouse, touchscreen, etc.

The memory 380 comprises auditory ability profile management logic 381 that may be executed to generate or update a recipient's auditory ability profile 383 that is stored in the memory 380. The auditory profile management logic 381 may be executed to obtain the results of objective evaluations of a recipient's cognitive auditory ability from an external device, such as an imaging system (not shown in FIG. 3), via one of the other interfaces 378(2)-378(N). In certain embodiments, memory 380 comprises subjective evaluation logic 385 that is configured to perform subjective evaluations of a recipient's cognitive auditory ability and provide the results for use by the auditory ability profile management logic 381. In other embodiments, the subjective evaluation logic 385 is omitted and the auditory profile management logic 381 is executed to obtain the results of subjective evaluations of a recipient's cognitive auditory ability from an external device (not shown in FIG. 3), via one of the other interfaces 378(2)-378(N).

The memory 380 further comprises profile analysis logic 387. The profile analysis logic 387 is executed to analyze the recipient's auditory profile (i.e., the correlated results of the objective and subjective evaluations) to identify correlated stimulation parameters that are optimized for the recipient's cognitive auditory ability.

Memory 380 may comprise read only memory (ROM), random access memory (RAM), magnetic disk storage media devices, optical storage media devices, flash memory devices, electrical, optical, or other physical/tangible memory storage devices. The processor 384 is, for example, a microprocessor or microcontroller that executes instructions for the auditory profile management logic 381, the subjective evaluation logic 385, and the profile analysis logic 387. Thus, in general, the memory 380 may comprise one or more tangible (non-transitory) computer readable storage media (e.g., a memory device) encoded with software comprising computer executable instructions and when the software is executed (by the processor 384) it is operable to perform the techniques described herein.

The correlated stimulation parameters identified through execution of the profile analysis logic 387 are sent to the cochlear implant system 100 for instantiation as the cochlear implant's current correlated stimulation parameters. However, in certain embodiments, the correlated stimulation parameters identified through execution of the profile analysis logic 387 are first displayed at the user interface 386 for further evaluation and/or adjustment by a user. As such, the user has the ability to refine the correlated stimulation parameters before the stimulation parameters are sent to the cochlear implant system 100.

The general operations for analysis of the recipient's auditory profile to identify correlated stimulation parameters that are optimized for the recipient's cognitive auditory ability have been described above. However, it is to be appreciated that the profile analysis logic 387 may operate in accordance with one or more selected guidelines set by a user via the user interface 386. For example, a user may configure the stimulation parameters that may be adjusted or set limits for how a stimulation parameter may be adjusted.

As noted above, the supplemental assessment of a recipient's cognitive auditory ability may include objective and subjective evaluations, or only subjective evaluations. When both objective and subjective evaluations are implemented, the supplemental assessment is generally performed in a clinical environment using, for example, a fitting system such as that shown in FIG. 3. However, when only subjective evaluations are used, the supplemental assessment may be performed in a remote environment using, for example, a computer, mobile phone, or other consumer electronic device.

Figure 4:
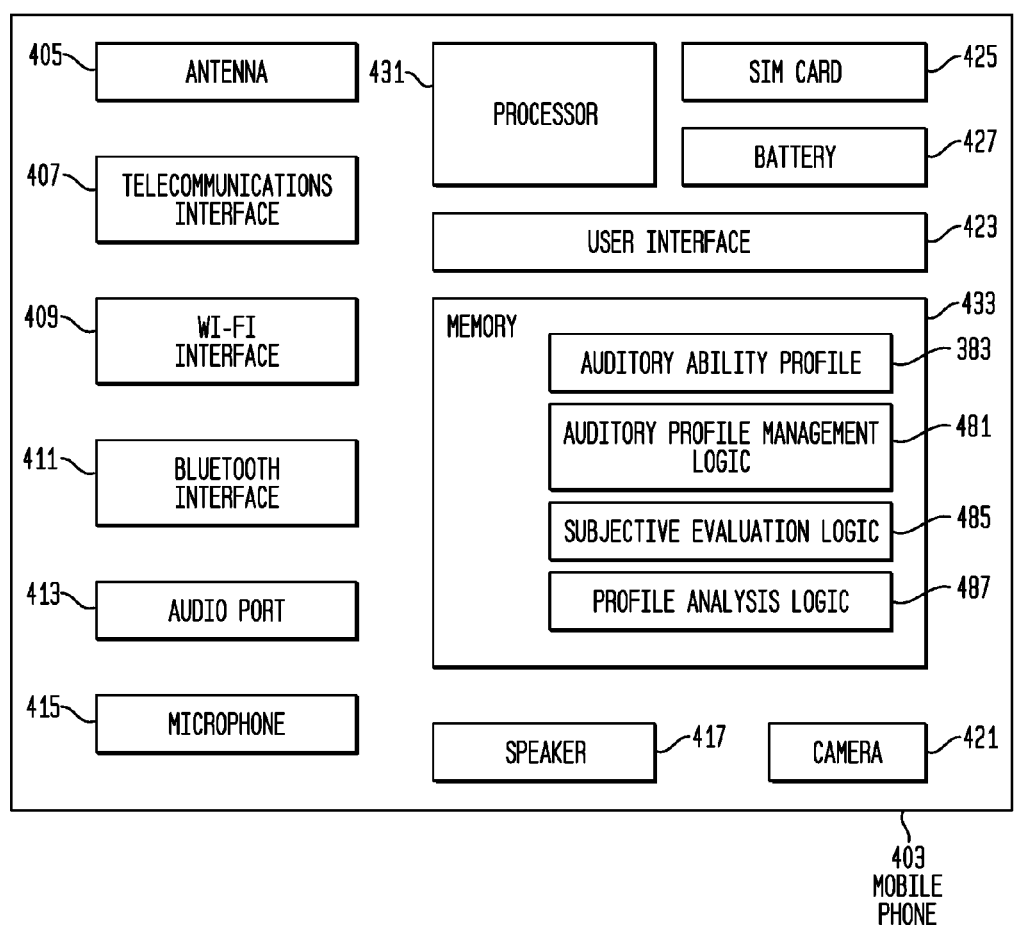
FIG. 4 is a block diagram of a mobile phone configured to execute techniques in accordance with embodiments of the present invention.

FIG. 4 is a block diagram of an illustrative arrangement for a mobile phone 403 in accordance with embodiments presented herein that is configured to perform subjective self-evaluations and, potentially, initiate changes to a recipient's correlated stimulation parameters. It is to be appreciated that FIG. 4 is merely illustrative and that supplemental assessments may be performed at other devices having different arrangements than that shown in FIG. 4.

Mobile phone 403 comprises an antenna 405 and a telecommunications interface 407 that are configured for communication on a wireless communication network for telephony services (e.g., a Global System for Mobile Communications (GSM) network, code division multiple access (CDMA) network, time division multiple access (TDMA), or other kinds of networks). Mobile phone 403 also includes a wireless local area network interface 409 and an infrared (IR) or Bluetooth® interface 411. The Bluetooth® trademark is owned by the Bluetooth® SIG. The wireless local area network interface 409 allows the mobile phone 403 to exchange data or connect to the Internet using, for example, 2.4 Gigahertz (GHz) Ultra high frequency (UHF) and/or 5 GHz Super high frequency (SHF) radio waves. The Bluetooth® interface 411 enables the mobile phone 403 to wirelessly communicate (i.e., directly receive and transmit data to/from another device via a wireless connection). In certain examples, the Bluetooth® interface 411 may be used to wirelessly connect the mobile phone 403 to the cochlear implant system 100 (FIG. 1). It is to be appreciated that the use of a wireless local area network interface in combination with a Bluetooth® interface is merely illustrative and that any other interfaces now known or later developed including, but not limited to, Institute of Electrical and Electronics Engineers (IEEE) 802.11, IEEE 802.16 (WiMAX), fixed line, Long Term Evolution (LTE), etc. interfaces may also or alternatively form part of the mobile phone 403.

Mobile phone 403 also comprises an audio port 413, one or more sound input elements, such as a microphone 415, a speaker 417, a camera 421, a user interface 423, a subscriber identity module or subscriber identification module (SIM) card 425, a battery 427, a processor 431, and a memory 433. Memory 433 comprises a copy of the recipient's auditory ability profile 383 and auditory ability profile management logic 481 that may be executed to update the recipient's auditory ability profile. The auditory profile management logic 481 may be executed to download a copy of the recipient's auditory ability profile from an external device, such as the fitting system 370, or the cochlear implant system 100 using, for example, one of the interfaces 407, 409, or 411. Memory 433 also comprises subjective evaluation logic 485 that is configured to perform subjective evaluations of a recipient's cognitive auditory ability and provide the results for use by the auditory ability profile management logic 481.

The memory 433 further comprises profile analysis logic 487. The profile analysis logic 487 is executed to analyze the recipient's auditory ability profile to determine if changes to the recipient's correlated stimulation parameters are appropriate and, in certain embodiments, initiate changes to the recipient's correlated stimulation parameters.

Memory 433 may comprise ROM, RAM, magnetic disk storage media devices, optical storage media devices, flash memory devices, electrical, optical, or other physical/tangible memory storage devices. The processor 431 is, for example, a microprocessor or microcontroller that executes instructions for the auditory profile management logic 481, the subjective evaluation logic 485, and the profile analysis logic 487. Thus, in general, the memory 433 may comprise one or more tangible (non-transitory) computer readable storage media (e.g., a memory device) encoded with software comprising computer executable instructions and when the software is executed (by the processor 431) it is operable to perform the techniques described herein.

Generally speaking, due in part to health/safety issues, a recipient is provided with a limited ability to initiate changes to his/her stimulation parameters. In one example, a recipient executes subjective evaluation logic 485 to perform a self-evaluation and the results of this self-evaluation are used by the auditory profile management logic 481 to update the recipient's auditory ability profile 383. The updated auditory ability profile 383 may then be analyzed by the profile analysis logic 487 to generate adjusted correlated stimulation parameters. These adjusted stimulation parameters may be uploaded to a database for evaluation and approval by a clinician or audiologist and, if approved, provided to the cochlear implant system 100 for instantiation. In another embodiment, the self-evaluation, profile update, and profile analysis, may be remotely monitored by a clinician or audiologist for real-time re-programming based on self-determined correlated stimulation parameters. In still other embodiments, the profile analysis logic 487 is only allowed to change a limited number of stimulation parameters, such as a recipient's threshold or comfort levels, which may be changed without approval of a clinician or audiologist.

In embodiments that utilize remote supplemental assessments of cognitive auditory ability, the results of the self-evaluations, profile updates, and profile analyses are uploaded to one or more databases to ensure alignment between the remote and clinical environments.

Figure 5:
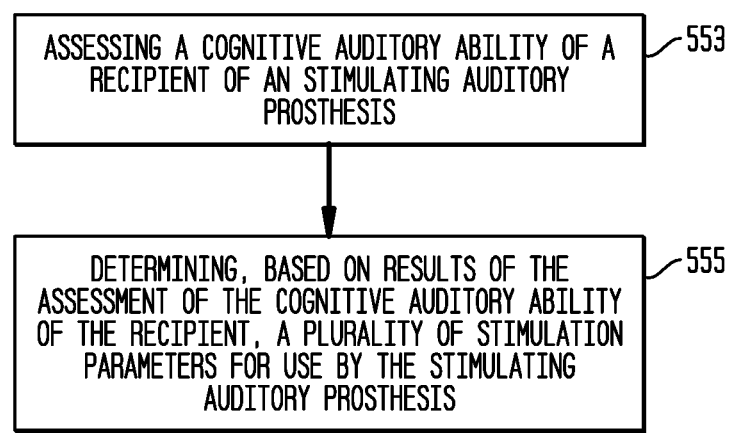
FIG. 5 is a flowchart of a method in accordance with embodiments presented herein.

FIG. 5 is a high-level flowchart of a method 551 in accordance with embodiments presented herein. Method 551 begins at 553 with the assessment of the cognitive auditory ability of a recipient of a stimulating auditory prosthesis. As described above, the initial or supplemental assessment of a recipient's cognitive auditory ability may include one or more objective evaluations configured to objectively quantify how the recipient's auditory brain areas have been affected by cross modal reorganization and/or one or more subjective evaluations configured to assess at least one of cognitive load or listening effort. In certain examples, the supplemental assessment of a recipient's cognitive auditory ability may be accompanied by sensory evaluations and/or hearing tests.

Returning to method 551, at 555 the results of the assessment of the cognitive auditory ability of a recipient are utilized to determine a plurality of stimulation parameters for use by the stimulating auditory prosthesis. The stimulation parameters are correlated to the cognitive auditory ability of the recipient such that electrical stimulation signals generated using the stimulation parameters, when delivered to the recipient, optimize an amount of electrical audio information presented to the recipient to the cognitive auditory ability of the recipient.

Figure 6:
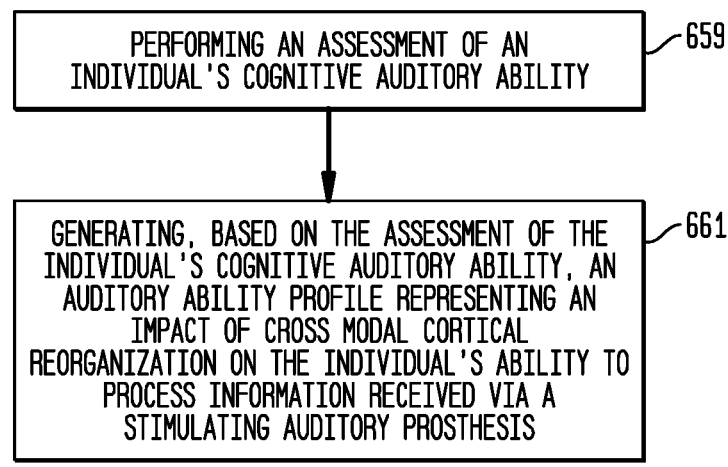
FIG. 6 is a flowchart of another method in accordance with embodiments presented herein.

FIG. 6 is a high-level flowchart of another method 657 in accordance with embodiments presented herein. Method 657 begins at 659 with the assessment of an individual's cognitive auditory ability. At 661, based on the assessment of the individual's cognitive auditory ability, an auditory ability profile is generated. The auditory ability profile represents an impact of cross modal reorganization on the individual's ability to process information received from via a stimulating auditory prosthesis.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   at one or more processors:
   assessing a cognitive auditory ability of a recipient of an electrically-stimulating auditory prosthesis to quantify an ability of auditory brain areas of the recipient to process electrically-provided audio information;

determining, based on the ability of the auditory brain areas of the recipient to process electrically-provided audio information, a plurality of stimulation parameters for use by the stimulating auditory prosthesis; and providing the plurality of stimulation parameters to the electrically-stimulating auditory prosthesis for instantiation at the electrically-stimulating auditory prosthesis.

2. The method of claim 1, further comprising:

generating, using the plurality of stimulation parameters instantiated at the electrically-stimulating auditory prosthesis, electrical stimulation signals that, when delivered to the recipient, optimize an amount of electrical audio information presented to the recipient to the cognitive auditory ability of the recipient.

3. The method of claim 1, wherein assessing the cognitive auditory ability of the recipient comprises:

performing at least one subjective evaluation configured to assess at least one of cognitive load or listening effort.

4. The method of claim 1, wherein assessing the cognitive auditory ability of the recipient further comprises:

analyzing how the recipient's auditory brain areas have been affected by cross modal reorganization in conjunction with one or more measures of cognitive load or listening effort to estimate the ability of the recipient's auditory brain areas to process electrical audio information.

5. The method of claim 4, wherein determining the plurality of stimulation parameters comprises:

matching a measure of the information expected to be presented by the stimulation parameters to a measure of the estimated ability of the recipient's auditory brain areas to process electrical audio information.

6. The method of claim 1, further comprising:

performing at least one sensory evaluation to identify functional sensory difficulties experienced by the recipient.

7. The method of claim 1, further comprising:

performing one or more hearing tests to generate results representing the performance of the stimulation parameters when in use by the stimulating auditory prosthesis.

8. The method of claim 1, wherein assessing the cognitive auditory ability of the recipient of the stimulating auditory prosthesis comprises:

performing, at a non-clinical location, a recipient initiated self-assessment of the cognitive auditory ability.

9. The method of claim 1, further comprising:

performing a supplemental assessment of the cognitive auditory ability of the recipient;

identifying a change in the cognitive auditory ability of the recipient; and adjusting the plurality of stimulation parameters based on the change in the cognitive auditory ability of the recipient.

10. The method of claim 9, wherein adjusting the plurality of stimulation parameters comprises:

adjusting the stimulation parameters to increase an amount of electrical audio information presented to the recipient with each set of stimulation signals generated using the stimulation parameters.

11. The method of claim 9, wherein adjusting the plurality of stimulation parameters comprises:

adjusting the stimulation parameters to decrease an amount of electrical audio information presented to the recipient with each set of stimulation signals generated using the stimulation parameters.

12. The method of claim 1, further comprising:

delivering selected sets of stimulation signals to effect rehabilitation of the recipient's cognitive auditory ability.

13. The method of claim 12, wherein delivering selected sets of stimulation signals to effect rehabilitation of the recipient's cognitive auditory ability comprises:

selecting dynamic stimulation parameters that are configured to adapt over time to provide increasingly dense spectral representations of sound in an adaptive manner so as to improve the recipient's cognitive auditory ability.

14. The method of claim 1, wherein assessing the cognitive auditory ability of the recipient comprises:

performing at least one objective evaluation configured to quantify how the recipient's auditory brain areas have been affected by cross modal reorganization.

15. A method, comprising:

at one or more processors:

performing an assessment of a cognitive auditory ability of a recipient of an auditory prosthesis;

generating, based on the assessment of the recipient's cognitive auditory ability, an auditory ability profile representing an estimated impact of cross modal reorganization on the recipient's ability to process information received via the auditory prosthesis;

determining, based on the estimated impact of cross modal reorganization on the recipient's ability to process information received via the auditory prosthesis, a plurality of stimulation parameters for use by the auditory prosthesis; and sending the plurality of stimulation parameters to the auditory prosthesis.

16. The method of claim 15, wherein performing an assessment of an individual's cognitive auditory ability comprises:

performing at least one subjective evaluation configured to assess at least one of cognitive load or listening effort.

17. The method of claim 15, wherein performing an assessment of an individual's cognitive auditory ability comprises:

performing at least one objective evaluation configured to objectively quantify how the individual's auditory brain areas have been affected by cross modal reorganization.

18. The method of claim 15, wherein generating the auditory ability profile comprises:

analyzing how the individual's auditory brain areas have been affected by cross modal reorganization in conjunction with one or more measures of cognitive load or listening effort to generate an estimate of the ability of the individual's auditory brain areas to process electrical audio information.

19. The method of claim 18, further comprising:

generating, using the auditory ability profile, stimulation parameters that are correlated to the estimated ability of the individual's auditory brain areas to process electrical audio information.

20. The method of claim 15, further comprising:

performing at least one sensory evaluation to identify functional sensory difficulties experienced by the individual.

21. The method of claim 15, further comprising:
determining, based on the auditory ability profile whether the individual is a candidate for a stimulating auditory prosthesis.

22. The method of claim 15, further comprising:
performing a supplemental assessment of the individual's cognitive auditory ability at a non-clinical location, wherein the supplemental assessment is initiated by the individual using a consumer electronic device; and
updating the auditory ability profile based on the supplemental assessment of the individual's cognitive auditory ability.

23. An apparatus, comprising:
a memory; and
one or more processors configured to:
obtain results of one or more evaluations of a cognitive auditory ability of a recipient of a stimulating auditory prosthesis,
generate, based on the one or more evaluations of the recipient's cognitive auditory ability, an auditory ability profile representing an impact of cross modal reorganization on the recipient's ability to process information received via the stimulating auditory prosthesis,
analyze the auditory ability profile to select a plurality of stimulation parameters for use by the stimulating auditory prosthesis, wherein the stimulation parameters are correlated to the cognitive auditory ability of the recipient; and
provide the plurality of stimulation parameters to the stimulating auditory prosthesis.

24. The apparatus of claim 23, wherein to obtain one or more evaluations of a cognitive auditory ability of a recipient, the processor is configured to:
perform at least one subjective evaluation that assesses at least one of cognitive load or listening effort.

25. The apparatus of claim 23, to obtain one or more evaluations of a cognitive auditory ability of a recipient, the processor is configured to
obtain the results of at least one objective evaluation that objectively quantifies how the recipient's auditory brain areas have been affected by cross modal reorganization.

26. The apparatus of claim 23, wherein to generate the auditory ability profile, the processor is configured to:
analyze how the recipient's auditory brain areas have been affected by cross modal reorganization in conjunction with one or more measures of cognitive load or listening effort to estimate the ability of the recipient's auditory brain areas to process electrical audio information.

27. The apparatus of claim 26, wherein to analyze the auditory ability profile to select a plurality of stimulation parameters for use by the stimulating auditory prosthesis, the processor is configured to:
match a measure of the information expected to presented by the stimulation parameters to a measure of the estimated ability of the recipient's auditory brain areas to process electrical audio information.

28. The apparatus of claim 23, wherein the processor is further configured to:
obtain the results of at least one sensory evaluation to identify functional sensory difficulties experienced by the recipient.

29. The apparatus of claim 23, wherein the processor is further configured to:
obtain the results of one or more hearing tests to generate results representing the performance of the stimulation parameters when in use by the stimulating auditory prosthesis.

30. The apparatus of claim 23, wherein the processor is configured to:
perform a supplemental assessment of the cognitive auditory ability of the recipient;
identify a change in the cognitive auditory ability of the recipient; and
adjust the plurality of stimulation parameters based on the change in the cognitive auditory ability of the recipient.

* * * * *